United States Patent
Cheynet

(10) Patent No.: US 7,944,204 B2
(45) Date of Patent: May 17, 2011

(54) IDENTIFICATION OF POINTS OF INTEREST IN A REGION OF THE SURFACE OF A PART AND APPLICATION TO THE OPTIMIZATION OF THE PATH AND OF THE ANGULAR POSITION OF EDDY CURRENT PROBES

(75) Inventor: Sandra Carole Angele Cheynet, Le Plessis Pate (FR)

(73) Assignee: SNECMA, Paris (FR)

( * ) Notice: Subject to any disclaimer, the term of this patent is extended or adjusted under 35 U.S.C. 154(b) by 420 days.

(21) Appl. No.: 12/128,373

(22) Filed: May 28, 2008

(65) Prior Publication Data
US 2008/0297149 A1 Dec. 4, 2008

(30) Foreign Application Priority Data
May 30, 2007 (FR) ...................... 07 55348

(51) Int. Cl.
*G01R 33/12* (2006.01)
*G01N 27/90* (2006.01)
*G01N 27/82* (2006.01)
(52) U.S. Cl. ...................... 324/262; 324/240
(58) Field of Classification Search .......... 324/202, 324/222, 223, 228, 229, 230, 231, 234, 238, 324/239, 240, 262
See application file for complete search history.

(56) References Cited

U.S. PATENT DOCUMENTS

| 3,736,543 | A | 5/1973 | Lademann et al. |
| 5,418,457 | A | 5/1995 | Hedengren et al. |
| 6,624,510 | B1 | 9/2003 | Chan et al. |
| 6,812,697 | B2 * | 11/2004 | McKnight et al. ............ 324/262 |
| 2003/0076310 | A1 | 4/2003 | Kanzaki et al. |

FOREIGN PATENT DOCUMENTS
FR 2 557 711 A1 7/1985
* cited by examiner

*Primary Examiner* — Kenneth J Whittington
(74) *Attorney, Agent, or Firm* — Oblon, Spivak, McClelland, Maier & Neustadt, L.L.P.

(57) ABSTRACT

Identification of points of interest in a region of the surface of a part, by bringing a surface reference into intimate contact with the region is disclosed. The surface reference includes a thin film sufficiently flexible to conform to the region and tracks made of electrically conductive material. The passage of an eddy current probe over a track delivers a significant signal representative of the track. This representative signal corresponds to a point of interest thus identified in the region. Thus, it possible to optimize the path and the angular position of an eddy current probe scanning a region of a part to be tested.

16 Claims, 1 Drawing Sheet

IDENTIFICATION OF POINTS OF INTEREST IN A REGION OF THE SURFACE OF A PART AND APPLICATION TO THE OPTIMIZATION OF THE PATH AND OF THE ANGULAR POSITION OF EDDY CURRENT PROBES

TECHNICAL FIELD

The invention relates to the identification of points of interest in a region of the surface of a part. Such identification of points of interest may advantageously be used in the field of nondestructive testing. In particular, it makes it possible to optimize the path and the angular position of an eddy current probe scanning a region of a part to be tested.

PRIOR ART

Testing using eddy currents is a method for the nondestructive testing of parts made of electrically conductive material. The test is carried out by means of a probe which comprises an electrical coil through which a sinusoidal current flows. When the probe, through which a sinusoidal current flows, is placed close to a part made of conductive material, the variable magnetic field produced by the coil induces eddy currents in the part. These eddy currents in turn create a magnetic field and there then exists magnetic coupling between the probe and the part to be tested, thereby modifying the impedance of the coil. By moving the probe over the surface of the part to be tested, it is possible to detect faults in the part (cracks, inhomogeneities, changes in conductivity, variations in geometry, etc.) by the variation in magnetic coupling between the probe and the part to be tested, this resulting in a variation in the impedance of the coil.

The angular position of the probe relative to the surface of the part to be tested causes the amplitude of the detection signal to vary in the same way as the distance of the probe from the part. The surface of the part to be tested must therefore be scanned by the probe orthogonally so that the intensity of the currents induced in the part is identical and optimal throughout the test.

The nondestructive testing of electrically conductive parts by eddy currents may be carried out on automatic machines, most particularly for checking the internal surfaces of hollow parts used in the aeronautical field. The scanning paths performed by these automatic machines on the surfaces to be checked have to be defined. At the present time, this poses many difficulties involved in delimiting the region to be checked and in verifying the angular position of the probe over the entire scan. In an attempt to alleviate these difficulties, programs are often carried out on oversized regions so as to guarantee overlaps. This results in a waste of time and in premature wear of the probes.

In principle, the optimal positioning of the probe may be checked by displaying the "lift-off", that is to say the lifting of the probe off the surface to be checked. However, this technique is impossible to apply in the case of automatic machines when differential-type probes are employed or if filters are used.

It is also possible to check the optimal positioning of the probe by a display method using endoscopic systems. The optimal positioning of the probe may also be checked by using scrapped parts with artificial defects in the region to be checked or by using scrapped parts with cuts made in them, making it possible to display the region to be checked. All these methods are expensive and rarely available to programmers.

SUMMARY OF THE INVENTION

The present invention makes it possible to remedy the drawbacks presented by the prior art. It is based on the identification of points of interest in a region of the surface of a part thanks to a surface reference and by means of an eddy current probe. One particularly advantageous application of the invention is in the checking of certain regions of metal parts by means of an eddy current probe. Thus, it is possible to identify points of interest within a region of a metal part free of defects and to check an identical region of another metal part on the basis of the identified points of interest. However, the identification of points of interest of a region can be used for other applications.

A first subject of the invention is a surface reference intended for identifying points of interest in a region of the surface of a part, said surface reference consisting of a thin flexible film capable of conforming to said region so as to be brought into intimate contact therewith, the thin film supporting tracks made of electrically conductive material, the material of the thin film, the material of the tracks and the geometry and distribution of the tracks being chosen so that, when the surface reference is in intimate contact with said region, the passage of an eddy current probe over a track delivers a significant signal representative of the track.

The material of the thin film may be an insulating material such as a fluoropolymer, for example chosen from polytetrafluoroethylene (PTFE), perfluoroalkoxy polymer (PFA) and fluorinated ethylene-propylene (FEP).

If the surface reference is intended for identifying points of interest in an electrically conductive region of the surface of the part (a metal part or a part made of an electrically conductive composite for example), the material of the tracks is advantageously chosen to have an electrical conductivity at least 20 MS higher than that of said region.

The material of the tracks may be chosen from gold, copper and silver.

Advantageously, the tracks consist of lines. These lines may be parallel to one another. They may also form a chequerboard grid pattern.

The thin film may be provided with an adhesive for bringing it into intimate contact with said region.

A second subject of the invention is a method of identifying points of interest in a region of the surface of a part, which comprises bringing a surface reference as defined above into intimate contact with said region, the method also including the passage of the eddy current probe over the surface reference and the recording of the signals representative of the tracks that are delivered by the probe, these representative signals corresponding to the points of interest thus identified in said region.

A third subject of the invention is a method of implementing an automatic check test for checking a region of the surface of identical metal parts by means of an eddy current probe, the method comprising:
  the identification, by the method of identification above, of
    points of interest in a region of the surface of a standard
    metal part, which is identical to the surface region of the
    metal parts to be tested and is free of defects, the iden-
    tified points of interest allowing the eddy current probe
    to scan the entire region of the standard metal part; and
  the recording of the position of the identified points of
    interest in the region of the surface of the standard metal
    part so as to be able to automatically check, by means of
    an eddy current probe, an identical metal part to be tested
    by repeating the scan carried out on the region of the
    standard metal part.

The identification of points of interest may then comprise the identification of start points in the region and of end points in the region so as to determine the path of an eddy current probe that has to scan the entire region.

This method may also include the recording, for each identified point of interest in the region of the surface of the standard metal part, of the angular position of the probe for which the signal delivered by the probe is optimal.

The invention applies in particular to the nondestructive testing of parts made of electrically conductive material, in particular to parts of aeronautical machines.

BRIEF DESCRIPTION OF THE DRAWINGS

The invention will be better understood and further advantages and features will become apparent on reading the following description, given by way of nonlimiting example, accompanied by the appended drawings in which.

DETAILED DESCRIPTION OF PARTICULAR EMBODIMENTS

The following part of the description deals, merely by way of example, with the identification of points of interest in a region of the surface of a metal part intended for an aeronautical machine.

Figure 1:
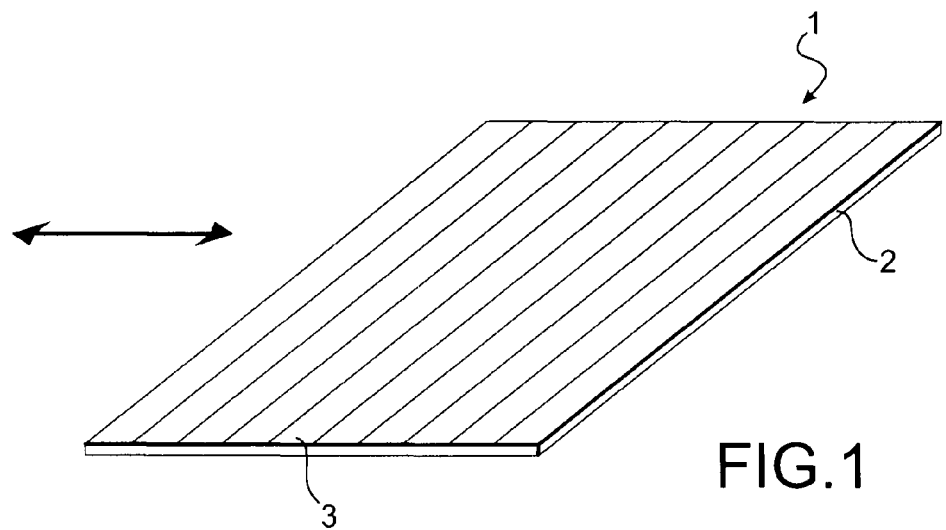
FIG. 1 is a perspective view of a surface reference according to the invention.

FIG. 1 is a perspective view of a surface reference 1 according to the present invention. The surface reference 1 is formed from a thin film or substrate 2 of small thickness (0.1 mm for example). The substrate 2 must be sufficiently thin and of uniform thickness so as to avoid gap problems. It must be sufficiently flexible to be able to match the profile of the part for which it is intended. Products sold under the trade mark Teflon® are very suitable. Polytetrafluoroethylene (PTFE), perfluoroalkoxy polymer (PFA) and fluorinated ethylenepropylene (FEP) may be mentioned. That face of the substrate 2 to be brought into contact with the metal part is advantageously self-adhesive and repositional.

Electrically conducting lines 3 are formed on the opposite face of the substrate 2 from the face to be brought into contact with the metal part. In the exemplary embodiment shown in FIG. 3, the conducting lines 3 are straight, parallel to one another and uniformly spaced apart. However, these lines could be curved. They could also be spaced apart nonuniformly. The conducting lines 3 may be distributed with a pitch of about 3 mm on the substrate 2. The pitch has to be adapted according to the size of the active region of the eddy current probe. A pitch of 3 mm is appropriate for an active probe region of 2 mm so as to avoid interference between the conducting lines.

The conducting lines 3 may be produced in various ways. Among the possible ways of producing these lines, mention may be made of the use of a kind of stencil, either for depositing gold (PVD process) or for applying silver lacquer, the use of very fine copper wires, the use of the process for forming copper lines used in flexible printed circuits, the use of silver screen printing and the use of conductive inks. The conducting lines 3 may be of different widths (for example 0.1 to 0.3 mm). Their thickness must be small (for example 0.05 mm) so as to avoid gap problems (a gap between the probe and the probed surface). The choice of material of the conducting lines is, in this application example, directly determined by the material of the metal part receiving the surface reference. This is because, to generate significant signals based on eddy currents, it is necessary to choose a conducting line material having an electrical conductivity very different from that of the metal part. Very good results may be obtained with a line conductivity at least 20 MS (megasiemens) greater than that of the metal part. To give an example, for a titanium part, the conducting lines may be made of copper.

Figures 2, 3:
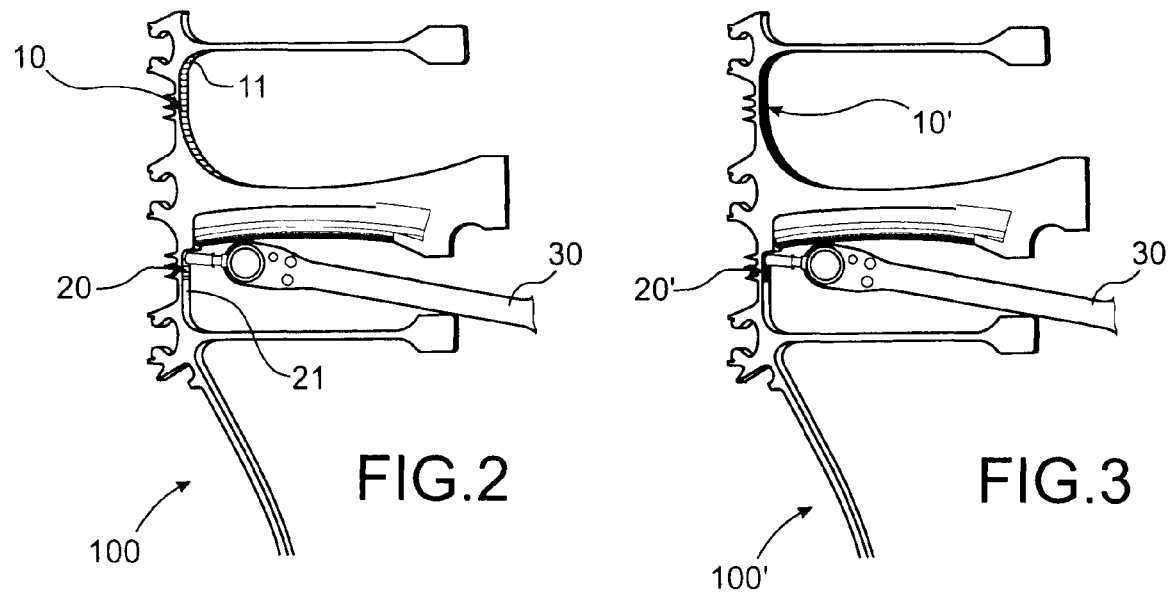
FIG. 2 illustrates the method of implementing a test for automatically checking a surface region of a metal part by means of an eddy current probe according to the invention.
FIG. 3 illustrates the application of the test method implemented according to the present invention.

FIG. 2 illustrates the method of implementing an automatic check test for checking a surface region of a metal part by means of an eddy current probe and a surface reference according to the invention.

The automatic check test is implemented by bringing the surface reference of FIG. 1 into intimate contact with a region of a standard metal part, i.e. one without any defects, said standard metal part being identical to the parts that have to be tested. The surface reference may be used to confirm the coverage of the region to be checked. Its size is then identical to the size of the region to be checked.

The surface reference is positioned precisely on the region of the standard part corresponding to the regions of the parts to be tested. In the case of blind regions, the use of an endoscope may prove necessary to verify that the surface reference has been positioned correctly. Once the surface reference has been correctly positioned, data acquisition from the region to be checked is started by an operator. The probe is moved transversely with respect to the conducting lines (see the double-headed arrow in FIG. 1). The variation in impedance of the coil of the measurement probe is recorded each time the line is passed. It is then possible to ensure coverage of the region by verifying that all the lines of the surface reference have been recorded. It is also possible to use the known spacings between the lines to determine the size of the region to be checked.

The path that the eddy current probe must follow so as to cover, by scanning, the entire region covered by the surface reference is then determined. To do this, the points of interest provided by the probe passing in succession over the conducting lines of the surface reference are recorded. When the probe has passed from one edge of the reference to the other, the probe is displaced by one pitch so as to travel another path from one edge of the reference to the other.

The surface reference may also be used to verify that the probe is orthogonal to the surface over which it travels. An optimal signal is recovered when the probe is orthogonal. This is important in the case of parts having regions to be checked that are not plane. To do this, the surface reference is characterized so as to determine the expected response each time a line is passed by a probe orthogonal to the deposited reference.

To characterize the surface reference, the latter is placed on a plate made of the same material as that of the part to be tested. The plate provided with the reference is positioned on an XY test bed. The plate provided with the reference is scanned by means of a probe having the same sensitive element as the test probe of the automatic machine, using the same parameters. The signals (amplitudes and/or phases) delivered by the probe upon passing the lines are recorded. The surface reference can then be used to optimize the positioning of the probe by analogy with the results obtained on a plane surface.

FIG. 2, already mentioned, is a partial sectional view of a complex metal part 100 serving as standard part. The regions 10 and 20 of the part correspond to regions that have to be checked on other parts. Surface references 11 and 21 respectively are deposited on the regions 10 and 20 and the data acquisition from the regions 10 and 20 by means of the eddy current probe 30 is initiated. The signals obtained as a result of the variations in conductivity allow the path followed to be checked and if necessary corrected, as explained above. In addition, a finer analysis is used to verify the positioning of the probe relative to the surface by analogy with the results obtained when characterizing the surface reference, or else by varying the position of the probe until a maximum amplitude is obtained on the deposited references.

FIG. 3 illustrates the application of the test method implemented according to the present invention on a part 100' to be tested that is identical to the standard part 100. The regions 10' and 20' may thus be checked using the test method established by the invention.

Surface references may be produced for each type of material checked by means of an eddy current probe. They may be produced in the form of a roll, from which it is sufficient to remove the desired length. They can be used on any type of surface (surface of revolution, plane surface).

The invention claimed is:

1. A system for identifying points of interest in a region of the surface of a part, comprising:
   an eddy current probe; and
   a surface reference, including:
      a thin flexible film capable of conforming to said region including a first face which is brought into intimate contact with said region, and
      tracks supported by the thin film and provided on a second face of the thin film, opposite the first face of the thin film, made of electrically conductive material,
   wherein the material of the thin film, the material of the tracks and the geometry and distribution of the tracks are chosen so that, when the surface reference is in intimate contact with said region, passage of the eddy current probe over the tracks delivers a significant signal representative of the points of interest in said region.

2. The system as claimed in claim 1, wherein the material of the thin film is an insulating material.

3. The system as claimed in claim 2, wherein the insulating material is a fluoropolymer chosen from polytetrafluoroethylene (PTFE), perfluoroalkoxy polymer (PFA) and fluorinated ethylene-propylene (FEP).

4. The system as claimed in claim 1, wherein, when the surface reference is intended for identifying points of interest in an electrically conductive region of the surface of the part, the material of the tracks is chosen to have an electrical conductivity at least 20 MS higher than that of said region.

5. The system as claimed in claim 1, wherein the material of the tracks is chosen from gold, copper and silver.

6. The system as claimed in claim 1, wherein the tracks include lines.

7. The system as claimed in claim 6, wherein the lines are parallel to one another.

8. The system as claimed in claim 7, wherein the lines are uniformly spaced apart.

9. The system as claimed in claim 1, wherein the first face of the thin film is provided with an adhesive for bringing it into intimate contact with said region.

10. The system as claimed in claim 6, wherein the lines form a checkerboard grid pattern.

11. A method of identifying points of interest in a region of the surface of a part, comprising:
   bringing a surface reference into intimate contact with said region, the surface reference including:
      a thin flexible film capable of conforming to said region, and
      thin film supporting tracks made of electrically conductive material;
   passing the eddy current probe over the surface reference; and
   recording the signals representative of the tracks that are delivered by the probe,
   wherein the representative signals correspond to the points of interest identified in said region.

12. A method of implementing an automatic check test for checking a region of the surface of identical metal parts by means of an eddy current probe, the method comprising:
   identifying points of interest in a region of the surface of a standard metal part as claimed in claim 11, the region of the surface of the standard metal part is identical to the surface region of the metal parts to be tested and is free of defects, the identified points of interest allowing the eddy current probe to scan the entire region of the standard metal part; and
   recording the position of the identified points of interest in the region of the surface of the standard metal part so as to be able to automatically check, by an eddy current probe, an identical metal part to be tested by repeating the scan carried out on the region of the standard metal part.

13. The method of implementing an automatic check test as claimed in claim 12, further comprising recording, for each identified point of interest in the region of the surface of the standard metal part, an angular position of the probe for which the signal delivered by the probe is optimal.

14. A method for nondestructive testing of parts made of electrically conductive material comprising:
   implementing an automatic check test as claimed in claim 12.

15. The method as claimed in claim 14, wherein the parts are for aeronautical machines.

16. The method of implementing an automatic check test as claimed in claim 12, in which the identifying of points of interest includes identifying start points in the region and end points in the region so as to determine the path of an eddy current probe that has to scan the entire region.

* * * * *